United States Patent [19]

Kahl et al.

[11] Patent Number: 5,149,801
[45] Date of Patent: Sep. 22, 1992

[54] BORONATED PORPHYRIN COMPOUNDS

[75] Inventors: Stephen B. Kahl, Portola Valley; Myoung-Seo Koo, San Francisco, both of Calif.

[73] Assignee: The Regents of the University of California, Oakland, Calif.

[21] Appl. No.: 616,679

[22] Filed: Nov. 21, 1990

[51] Int. Cl.$^5$ ............................................ C07D 487/22
[52] U.S. Cl. .................................... 540/145; 424/1.1; 514/410
[58] Field of Search ........................................ 540/145

[56] References Cited

U.S. PATENT DOCUMENTS 4,516,535  5/1985  Russell, Jr. et al. .................. 128/1.1
4,959,356  9/1990  Miura et al. .......................... 540/145
4,963,655 10/1990  Kinder et al. ......................... 530/331

OTHER PUBLICATIONS

Barth et al., "Boron Neutron Capture Therapy for Cancer", Scientific American, 100–107, Oct. 1990.
Coderre et al., "Selective Delivery of Boron by the Melanin Precursor Analogue p-Boronphenylalanine to Tumors Other Than Melanoma", Cancer Research, 50, 138–141, Jan. 1, 1990.
Delaney et al., "Photodynamic Therapy of Cancer", Comprehensive Therapy, 14, No. 5, 43–55, May 1988.
Fairchild et al., "In Vitro Determination of Uptake, Retention, Distribution, Biological Efficacy, and Toxicity of Boronated Compounds for Neutron Capture Therapy", Cancer Research, 50, 4860–4865, Aug. 15, 1990.
Fairchild et al., "Optimization of Boron and Neutron Delivery for Neutron Capture Therapy", Pigment Cell Research, 2, 309–318, 1989.
Finkel et al., "Distribution of $^{10}$B After Infusion of Na$_2$ $^{10}$B$_{12}$H$_{11}$SH Into a patient with Malignant Astrocytoma: Implications for Boron Neutron Capture Therapy", Neurosurgery, 24, No. 1, Jan. 6–11, 1989.
Hawthorne et al., "Preparation of Tumor-Specific Boron Compounds; 1. In Vitro Studies Using Boron-Labeled Antibodies and Elemental Boron as Neutron Targets" Journal of Medicinal Chemistry, 15, No. 5, 449–452, May 1972.
Joel et al., "Pharmacokinetics and Tissue Distribution of the Sulfhydryl Boranes (Monomer and Dimer) in Glioma-Bearing Rats", Strahlenther. Onkol., 165, 167–170, 1989.
Kahl et al., "New Tumor Localizers: Advances in the Use of Low Density Lipoproteins (LDL)" Strahlenther Onkol., 165, 137–139, 1989.
Mishima et al., "Treatment of Malignant Melanoma by Single Thermal Neutron Capture Therapy with Melanoma-Seeking $^{10}$B-Compound", The Lancet, 388–389, Aug. 12, 1989.
Miura et al., "Preparation of Carboranyl Porphyrins for Boron Neutron Capture Therapy", Tetrahedron Letters, 31, No. 16, 2247–2250, 1990.
Sneath et al., "Protein-Binding Polyhedral Boranes.1" Journal of Medicinal Chemistry, 17, No. 8, 796–799, 1974.
Wong et al., "Boron Hydride Derivitives for Neutron Capture Therapy.1", Journal of Medicinal Chemistry, 17, No. 8, 785–791, Aug. 1974.
Fairchild et al., "A Comparison of Particle Radiation Therapy Modalities", Chpt. 2 in Boron-Neutron Capture Therapy for Tumors, H. Hatanaka, editor, Nishimura, 1986.
Hatanaka, "Clinical Experience of Boron-Neutron Capture Therapy for Gliomas-A Comparison with Conventional Chemo-Immuno-Radiotherapy", Chpt. 25 in Boron-Neutron Capture Therapy for Tumors, H. Hatanaka, editor, Nishimura, 1986.

Primary Examiner—Mukund J. Shah
Assistant Examiner—Jyothsna Venkat
Attorney, Agent, or Firm—Majestic, Parsons, Siebert & Hsue

[57] ABSTRACT

A compound is described having the structure

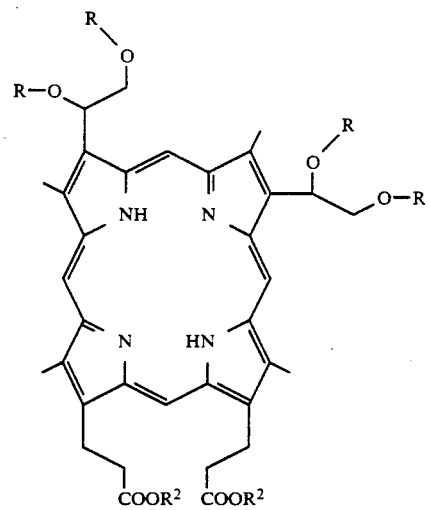

where R preferably is

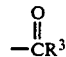

and most preferably R$^3$ is a closo-carborane and R$^2$ is —H, an alkyl or aryl having 1 to about 7 carbon atoms, or a physiologically acceptable salt. Compounds of the invention are useful in boron neutron capture therapy, photodynamic therapy, and other biomedical applications. One embodiment we have designated 2,4-bis-[α,β-(1,2-dicarbaclosododecaborane carboxy)ethyl]-deuteroporphyrin (x), appears not to pass through the normal blood brain barrier, has excellent water solubility, and has been shown efficacious in boron neutron capture therapy in vivo against the KHJJ mammary carcinoma.

7 Claims, No Drawings

BORONATED PORPHYRIN COMPOUNDS

This invention was made with Government support under NIH Grant No. CA-37961 awarded by the Department of Health and Human Services and under the Associated Universities Inc. Contract No. De-AC02-76CH00016 with the U.S. Department of Energy. The Government has rights in this invention.

FIELD OF THE INVENTION

The present invention generally relates to porphyrins and more particularly to porphyrins with glycol derivative substituents at pyrrole ring positions 2 and 4 where the substituents preferably have biological activity or are a fissionable or neutron-activatable nuclide, which compositions are useful in boron neutron capture therapy, photodynamic therapy, and other biomedical applications.

BACKGROUND OF THE INVENTION

A recent article in the Oct. 1990 issue of *Scientific American* by Barth et al. describes boron neutron capture therapy for cancer. The use of boron compounds in the treatment of human cancer is based on the unique affinity of nonradioactive $^{10}$B nuclei for thermal (low energy) neutrons. The major nuclear reaction occurring on slow neutron absorption by $^{10}$B gives an alpha particle of 1.47 MeV, a lithium atom of 0.84 MeV and a gamma ray of 0.48 MeV. One of the most attractive features of antineoplastic therapy involving such reactions is that reactants of very low energy (less than 1-2 KeV) are converted to cytotoxic products of approximately 2.8 MeV directly within the cancerous cell. Since the nuclear fragments produced by this fission reaction travel only about 10-15 micrometers or one cell diameter, destructive radiation predominates only in the immediate vicinity of cells containing significant $^{10}$B concentrations.

None of the normal elements comprising human tissue possess significant thermal neutron cross sections compared to $^{10}$B, although their high normal concentrations mean that some 10-15% of the neutron dose is absorbed in side reactions. These are principally the $H(n,\gamma)D$ and $^{14}N(n,P)^{14}C$ reactions as well as whatever fast neutron and gamma contaminants are present in the incident beam. Experience has shown that these contaminating gamma rays and fast neutrons can be removed, and appropriately filtered beams may be designed to give good neutron penetration to any desired depth to reach deep-seated tumor sites. Boron-10 has a thermal neutron cross section of approximately 4000 barns and a natural abundance of nearly 20%. Moreover, current technology permits relatively facile and inexpensive enrichment of boron compounds up to about 95% including the borane starting materials noted in this application. The thermal neutrons themselves are of subionizing energy and no significant effect from thermal neutron irradiation in human tissue has been noted in the literature.

The only requirements for effective clinical use of boron neutron capture theory (BNCT) in treating human cancer are: (1) a significant concentration of $^{10}$B in the neoplasm, historically estimated to be 10-20 μg of $^{10}$B per gram tissue (but potentially as low as about 1 μg), and (2) a ratio of tumor localized $^{10}$B to plasma $^{10}$B sufficient to avoid adverse effects on normal tissue in the immediate vicinity of the tumor, especially the vascular endothelium.

In the 50 years or so since the use of thermal neutron fissioning of $^{10}$B as a therapeutic modality was proposed, chemists have been faced with the challenge of developing boronated molecules which would specifically and selectively concentrate in neoplastic cells. Until fairly recently, this has proven to be a tantalizing but unattainable goal. None of the many boron compounds synthesized and evaluated during the period from 1950 through the early 1980's has been found to be truly suited for BNCT.

A resurgence of interest in selective targeting of boron compounds had occurred in the early 1970's. Several groups have since bound boron to antibodies in various forms, but generally found that the resultant conjugates either precipitated, could not be loaded with sufficient boron, or could not be purified Hawthorne, et al., *J. Med. Chem.* 15:449 (1972); Wong, et al., *J. Med. Chem.* 17:785 (1974); and, Sneath, et al., *J. Med. Chem.* 17:796 (1974).

The failure of efforts up to about 1980 resulted primarily from lack of tumor specificity and excessive blood boron concentration at the time of irradiation. Since 1980 a second resurgence of interest in the area occurred. This work has generally taken the form of attaching boron in some form to biological carriers specifically targeted to cancerous cells. $Na_2B_{12}H_{11}SH$ (BSH) is currently being utilized by Dr. Hiroshi Hatanaka, a Japanese neurosurgeon, in the treatment of upwards of 100 patients. His clinical studies of BNCT treatment of grade III-IV cerebral gliomas with this compound have shown five year survival rates of 30%, a figure far exceeding that obtained with conventional techniques. Hatanaka, *Boron neutron Capture Therapy for Tumors,* Nishimura (1986). BSH is currently being considered for clinical trials in the United States and Europe despite the fact that it does not show particularly strong preference for tumor cells of any type and almost certainly does not remain within or enter tumor cells for any significant time. Very recently another Japanese group, led by dermatologist Dr. Yutaka Mishima, has announced the successful treatment of eight cases of human malignant melanoma using p-boronophenylalanine (BPA) as the boron carrier. Mishima, et al., *Lancet* 2:388 (1989). This compound is tumor cell-targeted by virtue of the excessive uptake of aromatic amino acids by melanotic melanoma cells where it is believed to serve as a false precursor for melanin biosynthesis, though the available evidence suggests it is not a tyrosinase substrate. BPA appears to be taken up in therapeutic amounts by the KHJJ murine mammary carcinoma, the GS-9L rat glioma, and the human U-87 MG glioma xenograft in nude mice. This compound delivers only a single boron atom per unit carrier, must be given in massive doses, and crosses the blood-brain barrier to a significant extent making it inappropriate for BNCT of glioma.

Other American groups have reported the synthesis of boronated pyrimidines and nucleosides, monoclonal antibodies, chlorpromazines, and amino acids.

U.S. Pat. No. 4,959,356, issued Sep. 25, 1990, inventors Miura and Gabel describe boronated porphyrin compounds for use in BNCT, such as compounds of the formulas

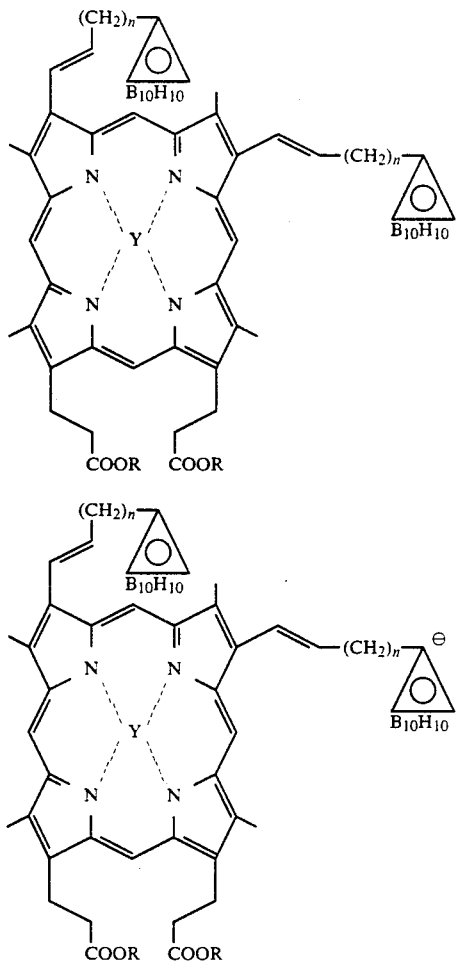

wherein R is hydrogen or lower alkyl having 1 to 6 carbon atoms and n is 0 to 10 and metal salts thereof. Similar is an article by Miura et al. *Tetrahedron Letters*, Vol. 31, No. 16, pp. 2247–2250 (1990). However, the boronated porphyrins described by Miura have vinyl carborane moieties that she reports as not being water soluble. Thus she must open the borane cages. But by opening those borane cages, one encounters significantly more toxicity for the compounds. Moreover, the resultant open-cage compounds are still not sufficiently water-soluble to enable administration without the use of adjuvant substances (e.g., polyethylene glycol). Also the compounds which Miura et al. describe are (at most) 19% boron by weight in the physiologically useful ($K^+$-salt) form. This is a disadvantage since limiting human doses may well be determined by the amount of porphyrin unit doses which may be tolerated.

U.S. Pat. No. 4,963,655, issued Oct. 16, 1990, inventors Kinder et al., describes compounds of the formula:

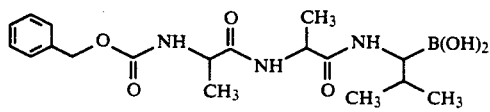

or physiologically acceptable salts thereof.

In addition to neutron capture therapy (NCT) generally and boron neutron capture therapy (BNCT) more specifically, additional uses of porphyrins in cancer therapies are those therapeutic strategies generally referred to as photodynamic therapy (PDT). A review article by Delaney and Glatstein in *Comprehensive Therapy*, pp. 43–55 (May 1988) describes this therapeutic strategy where a light-activated photosynthesizer can interact with ground state molecular oxygen to yield reactive oxygen species (via singlet oxygen). Since porphyrins of many structural types localize in a wide variety of malignant tumors, this localization has formed the basis for treatment of at least 3000 patients in the United States alone (twice that worldwide) over the past several years through PDT. Complete response (disappearance of tumor or biopsy proven) has occurred in a high percentage of patients in relatively advanced stages of skin, bladder, and lung cancers, and cancers of the reproductive system through photodynamic therapy.

Hematoporphyrin derivative (HPD) and Photofrin II composition, the PDT agents used to date in clinical trials, are complex mixtures of porphyrins. Aggregated hematoporphyrin dimer and trimers bound together with ester linkages appear to be the most likely structures o the tumor-localizing fractions of HPD when isolated by LH-20 gel filtration using organic solvents. Other evidence suggests that an ether linked oligomer fraction contributes significantly to the localizing fraction. Whatever the covalent linkage, these polymers have a very strong tendency to aggregate in aqueous media through non-covalent forces. This form is neither fluorescent nor an efficient singlet oxygen generator.

A variety of new drugs structurally related to porphyrins are being investigated for photodynamic therapy. Among these are phthalocyanines, chlorins, and purpurins. The phthalocyanines (PC) have received the greatest share of attention and have been found to be selectively retained by tumors, are resistant to chemical and photochemical degradation, are non-toxic, and are relatively easy to synthesize. PC's containing a fissionable or neutron-activatable nuclide were even proposed for treatment of brain tumors 25 years ago. Both in vivo and in vitro studies with sulfonated PC's indicate that tumor cell localization and photoinduced tumoricidal activity for several water-soluble PC's are similar to HPD. Particularly noteworthy is the lack of toxicity of various PC's in various species. Other compounds which have recently received attention as photosensitizers are chlorins and purpurins, and benzoporphyrins (BPD).

However, given the clear superiority of NCT to PDT in the treatment of many types of deep-seated tumors, it would appear that boronated porphyrins offer one of the best hopes for clinical use of NCT. Moreover, the lessons learned in NCT localization should be applicable to PDT, and vice versa, and in the case of boronated porphyrins might permit simultaneous use of both NCT and PDT.

A recent report by a blue-ribbon DOE panel concluded "There is a need for boron compounds which possess greater specificity for tumor, longer persistence and low systemic toxicity. Compound development of those structures which possess both specificity and persistence for tumor cells under in vivo conditions, while attaining low values in blood and continuous normal structure, is crucial. Rational syntheses of boron compounds and a well designed biological evaluation are important not only to determine concentration and persistence per se but to provide feed back to the synthetic chemist in the creation of new, more useful compounds." Report of the Health and Environmental Research Advisory Committee, (p. 20) S. Wolff, chair; Office of Energy Research, Department of Energy, 1990.

SUMMARY OF THE INVENTION

In one aspect of the present invention, a compound is provided having the structure

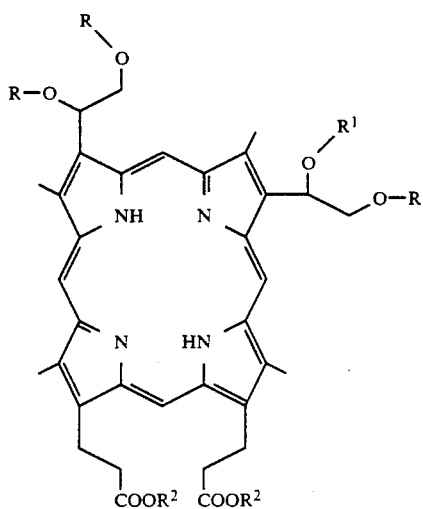

where R is

$R^1$ is —H or

$R^3$ is a carborane, and $R^2$ is —H, an alkyl or an aryl having 1 to about 7 carbon atoms, or a physiologically acceptable salt. Particularly preferred are wherein $R^3$ is a closo-carborane, such as 1,2-icosahedral closo-carborane and 1,7-icosahedral closo-carborane (substituted or unsubstituted). The particularly preferred embodiments can be administered in pharmaceutically acceptable, water-based solutions for biomedical applications such as boron neutron capture therapy (where $R^2$ is a physiologically acceptable salt, such as potassium) or can be conjugated with lipoprotein (preferable when $R^2$ is an alkyl or an aryl) and administered to a patient in photodynamic therapy.

In another aspect of the present invention, compounds such as illustrated above, or wherein $R^3$ includes other moieties, are prepared by contacting a porphine precursor compound with substituents on at least pyrrole ring positions 2 and 4, the substituents including a glycol with two hydroxyl groups, with an acid chloride having the structure

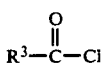

in the presence of a reaction rate enhancing amount of p-dimethylamino pyridine, to acylate at least one hydroxyl group of each glycol substituent and to form a porphine reaction product having a plurality of $R^3$ groups covalently bonded to a respective two pyrrole rings thereof. The use of DMAP as a "hyper-acylation" reagent to form tetra-ester products with even sterically hindered, relatively large $R^3$ groups (such as the closo-carboranes), is a powerful tool for preparing compounds useful in a variety of biomedical therapies

DETAILED DESCRIPTION OF THE PREFERRED EMBODIMENTS

Broadly, the invention relates to cellular drug delivery compositions and methods where the "delivery agent" can be viewed as built from a porphine precursor, whose basic structure is illustrated as Formula P:

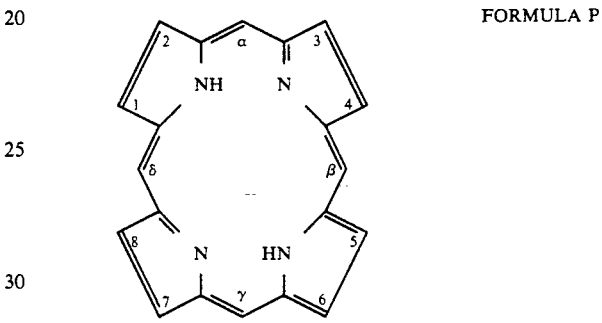

FORMULA P

Porphine, of course, is the parent (or core) substance of the porphyrins, which have side chains and methyl groups substituted for some hydrogens in the porphine pyrrole rings. Compounds of the invention have substituents on at least two of the pyrrole rings of porphine at pyrrole ring positions 2 and 4. These substituents at pyrrole ring positions 2 and 4 are derivatives of glycol. These derivatives are preferably wherein at least one hydroxyl group of each substituent is derivatized to include a moiety with biological activity (such as antineoplastic or tumor-uptake properties) or with a nuclide that is fissionable or neutron-activatable.

Preferred embodiments of the invention have the structure illustrated by Formula 1.

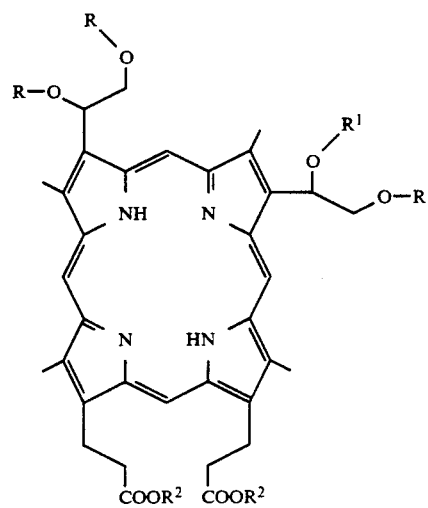

where R and/or $R^1$ is derived from an acid chloride having the structure

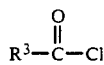

and $R^3$ preferably is a moiety with biological activity or with a fissionable or neutron-activatable nuclide. Particularly preferred embodiments of this invention are where $R^3$ is a carborane, and most preferred are closo-carboranes in a $^{10}$boron enriched form.

Compounds with boron cage systems in which one or more carbon atom is present as an integral part of an electron-delocalized boron framework are given the general name "carboranes", which term includes both closed polyhedra and open-cage structures. Carboranes are distinct from other organoboron species, such as the alkyl boranes, because the carbon(s) are part of the cage itself rather than present as a ligand. An early monograph on these electron-deficient boron cage compounds is by Grimes, *Carboranes*, Academic Press (1970), which describes nomenclature, structure, synthesis, and properties of carboranes, including those of interest for this invention. There are a series of stable polyhedral boron cage systems that have been isolated in at least one isomeric form. The symbol

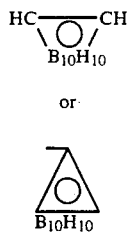

is often used in the literature to represent the icosahedral 1,2-$C_2B_{10}H_{12}$ isomer. Two particularly preferred cage system isomers for this invention are the 1,2-$C_2B_{10}H_{12}$ isomer and the 1,7-$C_2B_{10}H_{12}$ isomer (the latter sometimes represented as "$HCB_{10}H_{10}CH$").

Thus, particularly preferred for embodiments of the invention are wherein $R^3$ is a closo-carborane, and most particularly is the 1,2-icosahedral isomer or 1,7-icosahedral isomer, whether substituted or unsubstituted. An illustrative substituent is, for example, a carboxyl group, which may be desirable to aid in solubilizing the porphyrin compound, or assisting in increasing tumor uptake. The physical properties of the 1,2-icosahedral isomer and the 1,7-icosahedral isomer are similar, but preparation of the 1,7-icosahedral isomer in the preferred $^{10}$boron enriched form has been found to involve some additional steps.

The closo-carboranes are particularly preferred because the open-cage carboranes lead to significantly increased toxicity of what can otherwise be substantially non-toxic compounds. Closed-cage and open-cage systems are typically designated by the prefixes "closo-" and "nido-", respectively.

Returning to Formula 1, $R^1$ is hydrogen or another

moiety, and $R^2$ is hydrogen, an alkyl (having 1 to about 7 carbon atoms) or an aryl (having 6 or about 7 carbon atoms, e.g. benzyl), or a physiologically acceptable salt, such as calcium or potassium.

Conversion of the bis-glycol substituents to tetra-ester (that is, when both R and $R^1$ are

is surprising due to the size and steric hindrance considerations for preferred moieties. Where one desires to only obtain a di-ester (that is, with $R^1$ as hydrogen), then typical acylation agents, such as pyridine or trimethyl amine can be used; however, where one desires the tetra-ester, such as in preparing the particularly preferred embodiment we have coined as "BOPP", then the conversion of bis-glycol critically depends upon the use of p-dimethylaminopyridine (DMAP) as a hyper-acylation reagent.

The particularly preferred embodiment is especially useful for applications where a stable, quite water-soluble, substantially non-toxic compound with a large number of boron atoms (40) is desired. These boron atoms in the $^{10}$boron form serve as nuclides that emit alpha particles when bombarded with thermal or epithermal neutrons (for boron neutron capture therapy). In the potassium salt form, the BOPP embodiment is very water soluble and can be readily prepared in concentrations of at least about 10 mg/mL, yet the compound retains a high degree of lipophilicity. We also have designated this BOPP embodiment by the phrase "tetra-carborane carboxylate ester of 2,4-Di($\alpha,\beta$-dihydroxyethyl)deuteroporphyrin (IX)." The preferred embodiment of BOPP for use in BNCT utilizes $^{10}$B-enriched carborane. As this material is presently unavailable from commercial sources, it must be made from $^{10}$B-enriched $B_{10}H_{14}$. For the preparation of small quantities, such as used in our preliminary studies, the method of Todd is suitable and is incorporated by reference. Kutal, et al., *Inorganic Syntheses*, 11:19-23 (1968). This method involves the conversion of $^{10}B_{10}H_{14}$ to 1,2-bis-acetoxymethyl carborane by reaction with 2-butyne-1,4-diol diacetate followed by conversion to the 1,2-bis-(hydroxymethyl) carborane and in situ oxidation of the diol to the product 1,2-dicarbaclosododecaborane with $KMnO_4$. However, due to the potentially hazardous nature of this oxidation, synthesis of larger quantities of the compound by the method of Fein et al., *Inorganic Chemistry*, 2:115 (1963) is to be preferred, incorporated by reference. Briefly, this method involves reaction of $B_{10}H_{14}$ with acetylene in benzene or toluene in the presence of a Lewis base such as acetonitrile or diethyl sulfide. The preferred embodiment for PDT and other uses utilizes natural abundance $B_{10}C_2H_{12}$ which is commercially available.

The particularly preferred BOPP embodiment, in addition to utility in a method of treating a patient with a malignant tumor through BNCT (by administering to the patient a tumor-concentrating dose and then activating the inventive embodiment with neutrons to cause alpha particle emission) is also useful in PPT when sufficient photons (such as from a source that emits red light, to convert ground state molecular oxygen to singlet oxygen) irradiate the patient's tumor.

Other biomedical applications for compounds in accordance with the invention include diagnostic or therapeutic use for atherosclerosis. This is because the boron embodiments of the invention, particularly BOPP when conjugated with or encapsulated by lipoprotein such as an LDL-cholesterol fraction, have been found to localize in plaques of atherosclerosis patients. Once taken up by the plaques, methods such as laser angioplasty can be used to localize and diagnose the plaque areas through use of appropriate wavelengths of light.

Conjugates of inventive embodiments with lipoprotein can be simply prepared.

For delivery of an embodiment such as BOPP using low density lipoprotein as the carrier agent, either of two methods of complexation are preferred. For the first, human low density lipoprotein, isolated from fresh human plasma by preparative density gradient ultracentrifugation, is treated by the method described by Kahl and Callaway, *Strahlenther Oncol.* 165:137 (1989), incorporated by reference. In brief, this method involves removal of the native cholesterol ester core of LDL by a published procedure, Krieger et al., *Biol. Chem.*, 259:3845 (1979), also incorporated by reference, incubation of the delipidated LDL with a solution of BOPP-dimethyl ester in $CCl_4$ (6 mg/200 $\mu L$), removal of the $CCl_4$ by nitrogen flow, and solubilization of the reconstituted LDL in 10 mM tricine (pH 8.6). This procedure results in LDL particles containing approximately 300 molecules of BOPP-dimethyl ester per LDL particle. LDL reconstituted in this manner behaves in a fashion similar to native LDL and enters cells by receptor-mediated endocytosis.

The second method is simpler, but results in fewer molecules of the sensitizer per LDL particle. Human plasma is incubated at 37° C. with an aqueous solution of BOPP (in the potassium salt form; 4 $\mu M$) for 30 minutes. The plasma lipoprotein fractions are then separated by density gradient ultracentrifugation. Approximately 25% of the administered porphyrin is found bound to the LDL fraction, 20% to the VLDL, and 55% to the HDL fraction.

Where one desires to prepare porphyrin compositions of the invention for photodynamic therapy a very wide number of different moieties ($R^3$) can be used since it is the core porphine structure that is photoactive.

In using embodiments of the invention for neutron capture therapy, it is believed that the desired isotope may be administered so as to accumulate in the tumor in amounts potentially as low as about 1 $\mu g$ of $^{10}B$ isotope per gram tissue (equivalent to 1 ppm). To accumulate the desired amount of isotope in the tumor, compounds of the invention are generally administered by injecting patients with a dose of about 100 mg/kg body wt. of the compound in a pharmaceutically acceptable medium prior to subjecting the patient to the neutron beam. As will be understood, the amount of compound in accordance with the invention that one desires to accumulate in the tumor will depend upon the amount of boron-10 presently in the compound (with compounds enriched tp abpit 95% over the naturally occurring about 20% of $^{10}$boron being preferred) and with the neutron beam power used. While i.v. administration is preferred, i.p. administration can be used and it is believed that the BOPP dimethyl ester embodiment is suitable for oral administration. One can give the total to be administered as a single bolus of 100 mg/kg or in serial portions totalling about 100 mg/kg over a period of about 7 to 10 days.

At present, there is no consensus concerning an effective minimum to be accumulated in a tumor for photodynamic therapies, despite the treatment of at least 3000 patients in the United States alone. However, we believe that administrating as little as 10 mg/kg body weight may produce sufficiently high tumor porphyrin levels to be efficacious. In the U.S., 5 mg/kg of the known Photofrin composition is generally used; in other countries a higher dose is acceptable. The BOPP embodiment is much less toxic than the prior art Photofrin composition, and thus larger amounts can be administered.

Aspects of the invention will now be exemplified by the following examples, which are understood to be illustrative and not limiting.

Examples 1–4A describe the preparation of the particularly preferred embodiment of the invention in the 1,2-isomeric form that we have designated as "BOPP". The reaction scheme is diagrammatically represented in Example 5 along with mass spectrometric and spectroscopic structural evidence. Example 4B illustrates the preparation and structure of the 1,7-isomer of BOPP, and also illustrates a variety of other compounds (through $R^3$ variations) that have been made by following the principles of preparation as with BOPP and by using the core porphyrin precursor structure.

Examples 6–9 describe various in vivo experiments by several means of administration. These experiments demonstrate that a significant therapeutic effect was obtained through practice of the invention. While the efficacy is illustrated in these examples with the KHJJ mammary tumor line, which has a demonstrated radioresistance, we believe that the particularly preferred "BOPP" embodiment will behave in a similar manner with a wide variety of human carcinomas including, but not limited to, brain, mammary, lung, liver, pancreatic, colonic, bladder, prostate, cervix, and ovary.

Example 10 illustrates by in vitro data the encapsulation of BOPP by lipoprotein including LDL and the use of the conjugate in two different cell lines and demonstrates that excellent tumor uptake was easily achieved.

EXAMPLE 1

Synthesis of bis-glycol porphyrin dimethyl ester

Dried protoporphyrin dimethyl ester (4.4 g) was dissolved in 1.6 L of dioxane and 3.0 mL of pyridine in the dark. This solution was thoroughly bubbled with argon to remove oxygen. Osmium tetroxide (4.0 g) was dissolved in 200 ml argon-degassed diethyl ether and added to the dioxane-porphyrin solution. The solution was well stirred under Ar in the dark for 24 hours. Sodium sulfite (8.8 g) was dissolved in 160 mL distilled, argon-degassed water and added to the solution. The reaction was heated to 75° C. on a steam bath for 6 hours. The reaction solution was cooled to 53°–55° C. and filtered quickly through 1.5 L medium fritted funnel and washed with a small portion of dioxane. Filtrate was evaporated in vacuo and then 200 mL and 750 mL of water was added with stirring to crystallize the product. The crystals were filtered through 1.5 L medium fritted funnel and washed with 100 mL water. The filtered solid was suspended in 200 mL, 15% methanol/methylene chloride and 450 mL hexane added with stirring to complete crystallization. The procedure was repeated to remove impurities if necessary.

EXAMPLE 2

Synthesis of
2,4-bis-[α,β-(1,2-dicarbaclosododecaborane carboxy)ethyl]deuteroporphyrin (IX) dimethyl Carborane carboxylic acid was synthesized from $1,2-B_{10}C_2H_{12}$ by the method of Zakharkin et al., Akad. Nauk SSSR, *Ser. Khim.*, p. 1376 (1967) and Zakharkin et al., *Tet. Lett.*, p. 1147 (1964), incorporated by reference. Briefly, this method involves treatment of the o-carborane with one equivalent of n-butyl-lithium in benzene to produce the mono-lithio compound. This species is reacted with $CO_2$ to give the lithium salt of the carboxylate which gives the free carboxylic acid on acidifcation. Conversion to the acid chloride is also by the method of Zakharkin et al. using $PCl_5$ in toluene. Vacuum distillation of the reaction mixture gives the carborane-carbonyl chloride.

The bis-glycol porphyrin prepared as described by Example 1 (500 mg, 0.75 mmol) was dissolved in dry methylene chloride (200 mL), and the solution bubbled with argon. To the above solution o-carboranyl acid chloride (690 mg, 3.341 mmol) was added. The solution was stirred, and 4-dimethyl aminopyridine (DMAP) 371 mg, 3 mmol) was added to the solution. The solution was stirred at room temperature for one hour and poured into water. The organic layer was separated, washed with dilute hydrochloric acid three times, saturated sodium bicarbonate (3×), water (2×), and dried over sodium sulfate. Unreacted carborane carboxylic acid was removed from the bicarbonate washes by acidification and extraction with hexane or diethyl ether. The solution was filtered and evaporated in vacuo to yield a crude product. Three spots were obtained on analytical TLC plate by developing with 100% methylene chloride. The top spot is the tetracarboranyl porphyrin dimethyl ester, and the two slower spots are tri- and di-carborane esters, respectively. The tetracarboranyl porphyrin dimethyl ester was separated by filtering the methylene chloride solution of the crude products through a silica gel pad. The first mobile band was obtained by washing with 100% methylene chloride (110 mL) and evaporating to dryness. Crystallization from methylene chloride-hexane gave 849 mg. Isolated yield was 80-85%. We coined "BOPP" as a shorthand designation for the inventive embodiment whose preparation has just been described (in the dimethyl ester form).

The conversion of bis-glycol to tetra-ester critically depends upon the use of p-dimethylaminopyridine (DMAP) as a hyper-acylation reagent and upon its stoichiometric relationship with bis-glycol and acid chloride. The rate of formation of tetra-ester product in the absence of nitrogen base is extremely slow, if it occurs at all. We have found that when pyridine or trimethylamine (two other frequently used acylation agents) were used rather than the DMAP reagent, then the rate of tetra-ester formation was very slow when compared to use of DMAP. However, when one wishes to prepare the diester form rather than the tetra-ester, then these other acylation agents (such as TEA) should be used rather than DMAP.

EXAMPLE 3

Synthesis of
2,4-bis-[α,β-(1,2-dicarbaclosododecaborane carboxy)ethyl]deuteroporphyrin (IX)

To a solution of the tetracarboranylporphyrin dimethyl ester prepared as described in Example 2 (300 mg, 0.224 mmol) in 100 mL ether was added 25% hydrochloric acid (100 mL). The solution was stirred at room temperature overnight. The solution was washed with copious water (to dilute acid). The ether layer was separated, dried over sodium sulfate and evaporated in vacuo to give the tetracarboranyl porphyrin diacid inventive embodiment we designate in shorthand as "BOPP free acid." Quantitative yield.

EXAMPLE 4A

Synthesis of
2,4-bis-[α,β-(1,2-dicarbaclosododecaborane carboxy)ethyl]deuteroporphyrin (X)

The tetracarboranyl porphyrin diacid, or "BOPP free acid" prepared as described in Example 3, (150 mg) was dissolved in 20 mL THF and 15 mL water was added. The solution was passed through 1×10 cm cation exchange resin, 200-400 dry mesh. The eluate was evaporated to increase the ratio of water (up to 60/40 water/THF) and passed through ion exchange resin again. The final eluate was evaporated to dryness in vacuo. Quantitative Yield. The resulting dipotassium salt is well solubilized in water. We designated this inventive embodiment as "BOPP."

EXAMPLE 4B

Synthesis of 1,7 Isomer

The 1,7 closo- and other $R^3$ moieties carborane isomer of BOPP was prepared in the same manner using 1,7-carborane carbonyl chloride, but with the following difference. Thermal isomerization of the 1,2-carborane to the 1,7-carborane occurs at 450°-500° C. Grafstein and Dvorak, *Inorganic Chemistry*, 2:1128 (1963). Yields in this process approach 95% when a flow through pyrrolysis system is used in conjunction with an inert carrier gas. This approach is preferred for the conversion of $^{10}B$-enriched 1,2 isomer to the 1,7 isomer.

Other sterically hindered organic acid chlorides, such as those listed below, can be used to incorporate desired $R^3$ moieties in an analogous manner to Examples 1-4A. Thus, compounds in accordance with the invention were prepared as illustrated by Reaction Scheme 1 (where any of the variations shown by formulas B-D can be readily prepared), but where $R^3$ was

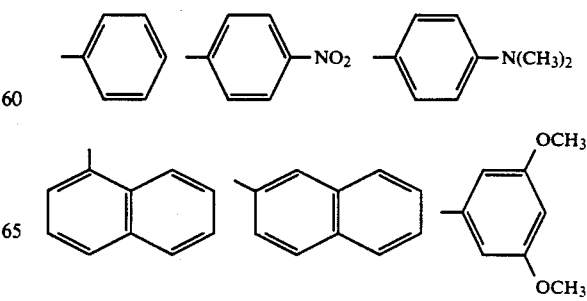

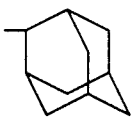

Characterization in all cases was by mass spectrometry, proton magnetic resonance, and UV-visible spectroscopy.

EXAMPLE 5

Diagrammatic representation of the reactions and structural formulas described in Examples 2–4A are illustrated by Reaction Scheme 1 where $R^3$ was the particularly preferred 1,2-icosahedral isomer ($^{10}$boron enriched) of a closo-carborane (here, unsubstituted).

retical molecular ion cluster of this formula is nearly identical to the 15-peak ion cluster observed at 1341. Similarly, LSIMS of the BOPP free acid produces a molecular ion cluster at nominal mass 1321 corresponding to the formula $C_{46}H_{79}B_{40}N_4O_{12}$ and whose shape is almost identical to the theoretical molecular ion cluster. In both mass spectra, four successive losses of $B_{10}H_{11}C_3O_2$ fragments are observed corresponding to loss of the carborane carboxylate. The visible spectrum of BOPP-dimethyl ester in $CH_2Cl_2$ (10 $\mu$M) consists of peaks at 404 (Soret) 502, 536, 572, and 624 nm.

A summary of the 300 MHz proton N.M.R. data for BOPP-dimethyl ester is presented in Table 1.

TABLE 1*

| δ | multiplicity | assignments |
|---|---|---|
| 10.27, 10.23, 10.16, 10.14 | s, 4H | meso H |
| 7.68 | m, 2H | α CH |

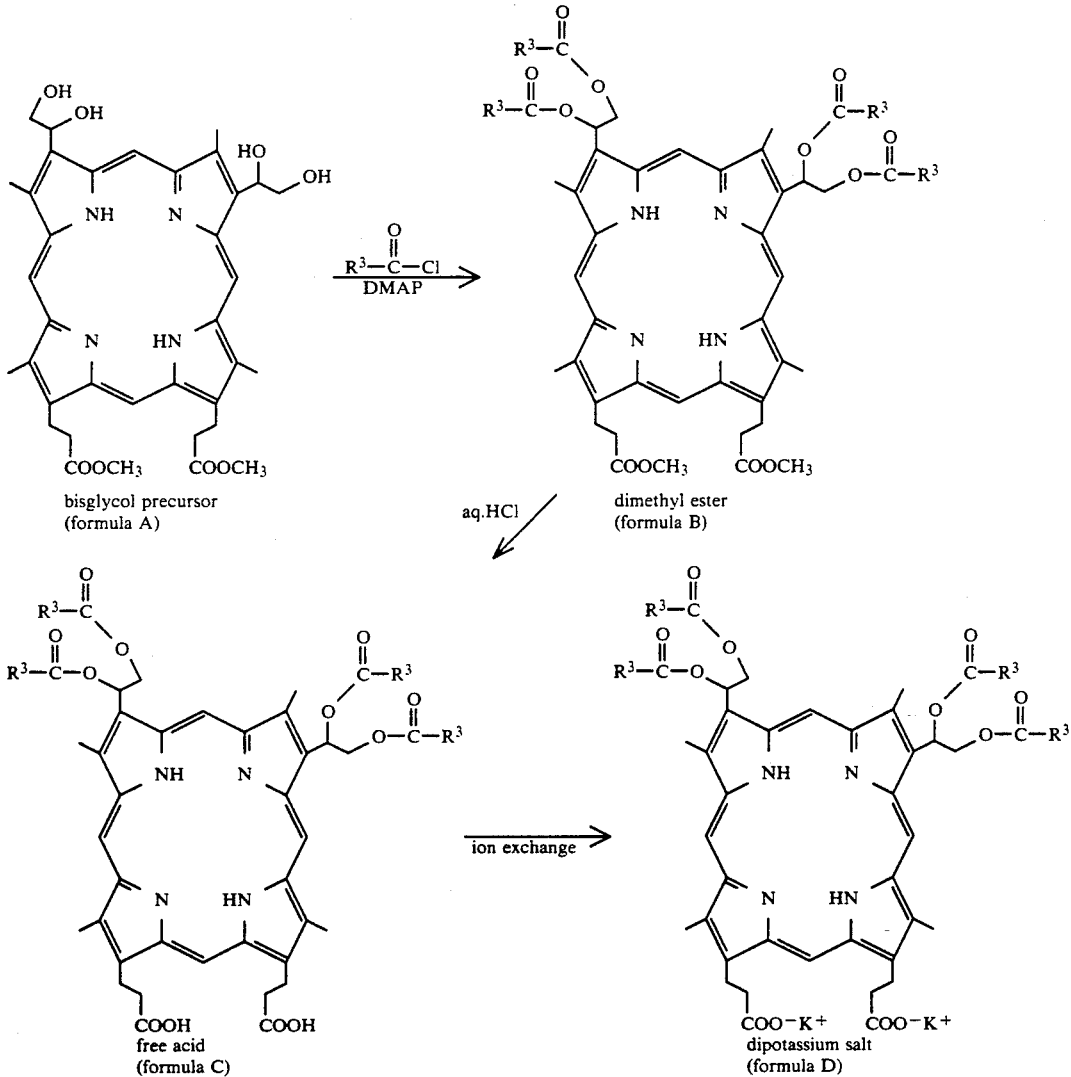

REACTION SCHEME 1 bisglycol precursor (formula A) → dimethyl ester (formula B) → free acid (formula C) → dipotassium salt (formula D)

Evidence in support of the structures prepared in Examples 2–4A and illustrated by Reaction Scheme 1 came from mass spectrometric and spectroscopic sources. The LSIMS mass spectrum of BOPP-dimethyl ester in a tetraethylene glycol matrix shows a molecular ion cluster (MH+) at nominal mass 1341 corresponding to the formula $C_{48}H_{83}B_{40}N_4O_{12}$. The shape of the theo-

| | | |
|---|---|---|
| 5.68; 4.99 | m, 4H | β $CH_2$ |
| 4.41 | m, 4H | Por-$CH_2$ |
| 4.17; 4.10 | s, 4H | carborane CH |
| 3.81; 3.80 | s, 6H | $CO_2CH_3$ |
| 3.68; 3.64 | s, 12H | β-$CH_3$ |
| 3.63; 3.61 | | |

TABLE 1*-continued

| δ | multiplicity | assignments |
|---|---|---|
| 3.30 | m, 4H | —$CH_2CO_2R$ |
| −3.65 | s, 2H | NH |

*N.M.R. spectrum was recorded in $CDCl_3$ (ca. 5 > $10^{-3}$ M) at 300 MHz at ambient temperature with TMS internal reference.

The lack of a molecular $C_2$ axis is clearly demonstrated by the presence of four, distinct resonances for the meso-H and $\beta$-$CH_3$ groups. This makes difficult a detailed analysis of the spectrum, especially the conformation of the carboranyl ester-bearing side chains. Nevertheless, several features are apparent. At least two distinct and equivalent carborane CH environments are present, perhaps a reflection of the primary and secondary alcohol ester functions. Three resonances are assigned to the two-carbon side chain protons, a chiral methine ($H_\alpha$), and pro-chiral methylene ($H_\beta$). The $H_\alpha$ assigned to 7.68 ppm is strongly deshielded by virtue of its being bound to a carbon bearing two strongly deshielding groups: the porphryin (ring current) and carboranyl acyl ($\sigma$ effects). The two $H_\beta$ resonances have significant (0.7 ppm) chemical shift differences which might arise if the most stable configuration forces one of the $H_\beta$ protons into a position over the porphyrin ring when it is subject to ring current deshielding relative to the other.

There are three possible configurations for the groups bound to the ethyl side chain, two gauche and one anti. Computer modeling based on the crystal structure of mesoporphyrin IX dimethyl ester suggests that the anti-configuration should offer the least amount of steric hindrance for all functional groups. The $\alpha$-carborane ester points down at an angle of about 45° C. and away from the porphyrin while the $\beta$-ester points up and over the porphyrin. This configuration also places one of the pro-chiral $H_\beta$ protons in a pocket formed by the porphyrin plane, a meso-H and the $O_\alpha$, giving rise to its potential deshielding relative to the other $H_\beta$. However, one gauche configuration also provides some side chain flexibility and deshielding of one $H_\beta$ from a similar pocket. In the remaining gauche form, all J—J coupling constants should be large and modeling indicates significant steric hindrance for the $O_\beta$.

normal brain ratios exceeding 150:1 were found for doses for 50, 100, and 150 mpk.

Consequently, we believe that BOPP does not pass through the normal blood brain barrier and is thus an exceedingly tumor selective drug. No gross toxicity has been found with BOPP when given by single i.v. injection at doses up to 200 mpk. When given to rats and mice either by serial intraperitoneal injection or intravenous, maximal tumor uptake occurs at approximately 24-36 hours post-administration. Maximal tumor-to-normal tissue and tumor-to-blood ratios occur at approximately 48 hours; however, therapeutic levels of BOPP persist in tumor for a week or more and are largely cleared from normal tissue and blood. BOPP does produce some skin photosensitivity.

EXAMPLE 7

BOPP is efficacious in BNCT in vivo against the KHJJ mammary carcinoma. BOPP was given at a dose of 150 mg/kg either i.v. or i.p. Two modes of therapy were evaluated; therapy was delivered in a single acute dose and also in 3 fractions. Two experiments in each mode were carried out. Each experiment consisted of ~10 animals. Evaluation of biological efficacy was based on determination of growth delay relative to unirradiated, undrugged controls. In order to avoid variations induced by differences in tumor volume at the start of therapy, tumor growth delay was determined by the time necessary to obtain a tumor volume 8 times that at the start of irradiation. Drug alone produced no growth delay. When compared to a neutrons alone, BNCT increased growth delay by 80% for a single acute doses, and by 125% for fractional therapy If one compares neutron capture therapy (NCT) in total (i.e., the boron reaction plus background radiation), the growth delay was increased by factors of 4.6 fold and 5.4 fold for single actue and fractionated therapy, respectively.

EXAMPLE 8

The biodistribution and BNCT efficacy of BOPP was studied. Table 2 summarizes the organ distribution of BOPP at 135 mg/kg dose given i.p. and at 5 different time points.

TABLE 2

| 135 mg BOPP/kg | tumor | blood | liver | muscle | spleen | adrenals | brain | kidneys |
|---|---|---|---|---|---|---|---|---|
| 6 hr | 22.5 | 21.2 | 90.6 | 16.2 | 70.8 | 101.0 | 1.1 | 54.3 |
| 24 hr | 30.2 | 17.4 | 104.3 | 14.3 | 67.2 | 125.9 | 1.0 | 63.0 |
| 48 hr | 22.1 | 9.6 | 73.3 | 10.1 | 60.8 | 127.4 | 0 | 53.0 |
| 72 hr | 24.7 | 8.3 | 64.4 | 6.9 | 41.4 | 95.3 | 0 | 42.9 |
| 120 hr | 20.0 | 7.6 | 82.1 | 10.3 | 39.1 | 93.1 | 0 | 52.9 |

EXAMPLE 6

In a stereotactically implanted murine brain tumor, administration of 100 mg/kg (mpk) of BOPP by a single intravenous injection resulted in tumor porphyrin levels of approximately 200 μg/g at 24 hours post-injection. This converts to a tumor boron content in the 60 μg/g range, roughly 6 times that needed for boron neutron capture therapy (BNCT). Tumor-to-normal brain ratio at this time is ~240:1 and rises to ~400:1 at 48 hours post-injection. Concurrent tumor-to-blood ratios are ~7:1 (24 hours) and ~11:1 (48 hours). At this dose, therapeutic tumor boron concentration is still present at 4 days, the longest time point taken, and is likely present for much longer. For intraperitoneal injection, tumor/-

Mice bore a KHJJ mammary carcinoma on the flank. BOPP was given by i.p. injection over a 5-day period in 5 equal doses to give the total dose indicated. Each point represents 3 mice except as noted; standard deviations are ~±20%. Especially noteworthy are the 120 hour (5-day) clearance points indicating the exceptional persistence of tumor boron levels. Lower liver and blood boron levels are possible using i.v. administration. Essentially no brain boron is found; the 6 and 24 hour points are likely rom blood in brain capillaries. From data studying the tumor/blood boron ratio for intraperitoneal injections at 105 and 135 mpk, substantial blood clearance and even higher tumor/blood ratios should be possible at longer clearance times, e.g. 7-14 days.

EXAMPLE 9

A series of individual experiments generally having about 6 animals (mice) in each component (unirradiated and undrugged controls; undrugged and irradiated; and drugged and irradiated) were undertaken. In general, 3 mg of BOPP was administered per mouse. This amount provides a total boron dose of about 45 μg $^{10}$B per g of body mass. The compound was easily dissolved in either sterile water or 5% glucose, and was administered both by i.p. injection and i.v. infusions. For i.p. administration, BOPP was administered at a concentration of 1 mg BOPP/mL, over a 2 day period: 3 injections per day were given, with a volume of 0.5 mL/injection. For i.v. infusions, the concentration was reduced to 0.5 mg BOPP/mL, and infused at the rate of 2 mL per day for 3 days. Irradiations were carried out 3 to 5 days post injection to allow clearance from normal tissues. All the experiments were carried out under conditions which minimized ambient light in order to avoid possible effects of photosensitization.

The KHJJ tumor line in BALB/c mice, derived from mammary tumor, was chosen (in part) due to its demonstrated radioresistance (TCD=53.5±5 Gy). Observation on a total of 106 treated mice carrying KHJJ tumors were analyzed: 62 were treated with reactor irradiation only, and 44 with irradiation plus BOPP. Two modes of therapy were evaluated: therapy delivered either in a single acute high dose rate exposure, or in multiple fractions (3 to 5) at high dose rate. In the first experiment the tumor growth after a single acute exposure (6.1 MW minutes) was studied in mice after i.p. administration of BOPP (and also in undrugged controls). Table 3 summarizes the data.

bient light. Studies carried out in vitro have demonstrated no sensitization due to high energy electromagnetic radiations ($^{137}$Cs γ-rays).

The analysis of tumor growth delay was based on the period between the first irradiation and the time the tumor increased by a factor of 10 in volume (to 10 $V_o$). Volume was determined by daily measurements of tumor length (l), width (w), and thickness (h), and corrected for a hemi-ellipsoidal shape using the formula V=0.524 lwh. The data after the initial growth retardation of each animal was fitted with an exponential function of time. The tumor growth rate of untreated animals depends on $V_o$, as given in Equation 1:

$$V = V_o e^{(0.35-0.50 V_o)t}$$

The growth delay ratio or GDR is the ratio of time to reach 10 $V_o$ for treated animals, relative to the same parameter for the irradiated control. Therefore, the GDR was determined for each animal, relative to an unirradiated control with an identical initial value $V_o$, as determined with Equation 1.

Boron Analysis. The distribution of BOPP in whole body tissue sections of mice was evaluated using whole-body neutron capture radiographic (WBNCR) techniques. Absolute amounts of boron in tissues were determined by prompt-gamma neutron activation analysis techniques.

Dosimetry. Foil activation measurements showed that the mouse thigh caused a significant perturbation of the thermal neutron treatment field. Back-scattering from the thigh (scattering mean free path length about 8 mm) produced a 20% increase in the entrance fluence rate and a decrease in the fluence rate φ (in m$^{-2}$ s$^{-1}$)

TABLE 3

| Exp. No. | No. of Animals | Irradiation time (MW-min) | No. of Fractions | Mode of Compound Administr. | $^{10}$B Administr. (1 g/gbm) | Initial Volume (mm$^3$)* | Growth Time+ (days)+ | Growth Delay++ Ratio+ |
|---|---|---|---|---|---|---|---|---|
| 1a | 23 | 6.1 | 1 | — | — | 140 ± 13 | 18.0 ± 9 | 2.19 ± .13 |
| 1b | 8 | 6.1 | 1 | ip | 39 | 169 ± 34 | 31.2 ± 3.5 | 3.69 ± .55 |
| 2a | 21 | 6.4 | 3 | — | — | 74 ± 13 | 17.6 ± 8 | 2.41 ± .12 |
| 2b | 10 | 6.4 | 3 | iv | 49 | 107 ± 24 | 28.2 ± 2.6 | 3.82 ± .40 |
| 2c | 7 | 6.3 | 4 | iv | 43 | 166 ± 18 | 22.9 ± 2.1 | 3.04 ± .27 |
| 3b | 7 | 7.4 | 4 | iv | 45 | 28 ± 4 | 36.0 ± 1.9 | 4.52 ± .24 |
| 4a | 18 | 10.3 | 5 | — | — | 50 ± 5 | 22.5 ± 1.5 | 3.27 ± .21 |
| 4b | 12 | 10.3 | 5 | iv | 37 | 43 ± 4 | 44.5 ± 1.5 | 6.33 ± .22 |

*Time required for 10× increase of the initial tumor mass from first treatment day.
+Ratio of the time required for 10× increase of the initial tumor mass in treated mice relative to that in untreated mice with similar initial mass.
++Average value ± standard error.

In the second experiment the exposure (6.5 MW minutes) was fractionated either on days 0, 2, and 4 (2.13 MW-minute per fraction) as in experiment 2b, or on days 0, 2, 4, and 7 with 3.2, 1.06, 1.06, and 1.06 MW min respectively, as in experiment 2c. In experiment 3, only drugged mice were irradiated on days 0, 2, 4, and 17 (2.12, 2.12, 2.12, and 1.03 MW minute respectively). In experiment 4a, a five fraction scheme was applied on day 0, 3, 5, 7, and 11 at 2.06 MW minute per fraction. The parameters of each experiment described here are also summarized in Table 3.

Data Analysis. Evaluation of the biological efficacy of the treatments (irradiated drugged or undrugged mice) was based primarily on the determination of the tumor growth delay relative to matched controls (no drug, no irradiation). Only growing tumors were considered in the present study. Studies both in vitro and in vivo have not shown any lethality or delay in growth due to BOPP alone under conditions of minimized amwith depth d (in m) in the thigh, approximated by the Equation 2:

$$\phi = 1.3 \cdot 10^{14} e^{-145 d}$$

The average $^{10}$B concentration was assumed to be 20 ppm for both i.v. and i.p. administration, according to biodistribution data. The use of the collimator reduced the thermal neutron fluence at the shielded parts of the mouse by three orders of magnitude. Only minor reductions were achieved in the other dose components; the fast neutron dose at 4 cm from the center of the treatment field was reduced by 20%, and no change was measured in the photon dose rate. The biologically effective wholebody dose is estimated to be −45 rads x RBE/MW-min (mouse midpoint).

Therapeutical Effectiveness. Results of all the various experiments are summarized in Table 3, along with the parameters applicable for each experiment (number of animals treated, initial tumor volume, irradiation conditions, and amount and mode of $^{10}$B administered).

Tumor growth delay relative to unirradiated controls was observed in all the experiments with the delay being significantly greater from neutrons and BOPP relative to neutron alone (experiments 1, 2, and 4). The data in ..this series of experiments did not indicate any clear difference between fractionated and single acute irradiations for the induction of GDR. The therapeutic gain achieved by the porphyrin (BOPP) administration can be expressed as an increase in the GDR, relative to undrugged irradiated animals. For example, in experiment 1, treatment with BOPP and neutrons extended the time required for tumor growth by a factor of 3.7, relative to a factor of 2.2 for neutrons alone, thus producing an increase of −70% in the growth delay ratio. Similar increases were found in the other experiments.

Under the assumption that multiple linear regression can be applied between GDR, the irradiation time (in MW min) and the amount of $^{10}$B administered (in μg $^{10}$B/gbm), it was found that the growth delay ratio (GDR) can be described by Equation 3:

GDR=0.996 exp (0.127 MW min+0.012 C)

where C is the $^{10}$B concentration. The correlation coefficient r=0.982. Therefore, GDR was found to increase exponentially with dose to the tumor, and the influence of 10 μg $^{10}$B/gbm administered to the animal was similar in effect to an increase in irradiation by about 1 MW-min.

In experiment 1 (Table 2), as well as other (n+ $^{10}$B) therapy experiments, it was noted that "cratering" of the tumor occurred, followed by scabbing and crusting of the skin surface. Animals receiving neutrons alone also showed such reaction. In order to determine if the irradiation itself was producing skin lesions, five non-tumor bearing mice were exposed for 1.8 MW min in a single acute dose (2.7 Gy of densely ionizing particles and less than 1 Gy of photons). The skin response was graded on a scale in which a score of 1 indicates erythema, and 2 to 3 indicates moist desquamation of varying severity. The skin response indicated that the cratering noted was, in fact, a response of the tumor to the irradiation.

It is clear from the these experiments that the presence of BOPP produced a significant therapeutic effect, as for example in experiment 4, where the GDR was extended by almost a factor of 2, from 3.3 (neutrons alone) to 6.3 (neutron+BOPP). Using Equation 3, it can be estimated that the administration of 45 μg $^{10}$B/gbw produces tumor growth retardation similar to that from 4 MW-min of beam alone (i.e., ~1.3 Gy of densely, ionizing particles, accompanied by ~0.5 Gy of sparsely ionizing particles).

EXAMPLE 10

BOPP was incubated (4 μm) with fresh human plasma for 30 minutes at 37° C. The plasma lipoprotein fractions were then isolated by density gradient preparative ultracentrifugation and examined for porphyrin content by UV-vis spectrometry. Approximately 55±10% of the administered porphyrin bound to the HDL protein fraction, 25% to LDL and the remaining 20% to VLDL. These three fractions contained 90±10% of the total porphyrin.

We have examined the in vitro uptake of a BOPP-LDL conjugate in human colonic carcimona (LoVo) and human hepatocyte (Chang) cell lines. Both lines are known to express high levels of the LDL receptor. Cell uptake and distribution was observed through microspectrofluorimetric analysis and high sensitivity image analysis. Intracellular boron concentrations exceeding 200 μg $^{10}$B/g were easily achieved.

It is to be understood that while the invention has been described above in conjunction with preferred specific embodiments, the description and examples are intended to illustrate and not limit the scope of the invention, which is defined by the scope of the appended claims.

We claim:

1. A compound having the structure

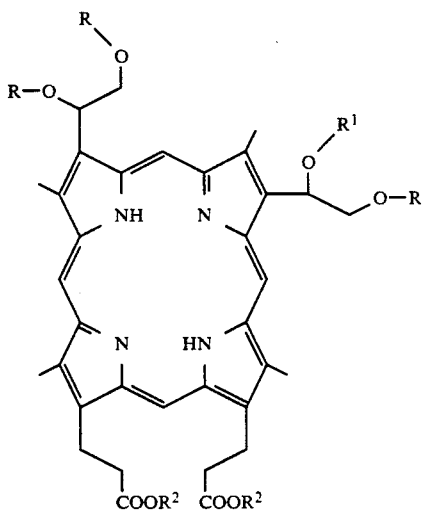

where R is

$R^1$ is —H or

$R^3$ is carborane, and $R^2$ is —H, an alkyl having 1 to 7 carbon atoms or an aryl having 6 to about 7 carbon atoms, or a physiologically acceptable salt.

2. The compound as in claim 1 wherein $R^3$ is a closo-carborane.

3. The compound as in claim 1 wherein $R^1$ is

4. The compound as in claim 2 or 3 wherein the carborane is 1,2-icosahedral isomer.

5. The compound as in claim 2 or 3 wherein the carborane is 1,7-icosahedral isomer.

6. The compound as in claim 4 wherein $R^2$ is potassium or sodium.

7. A compound having the structure

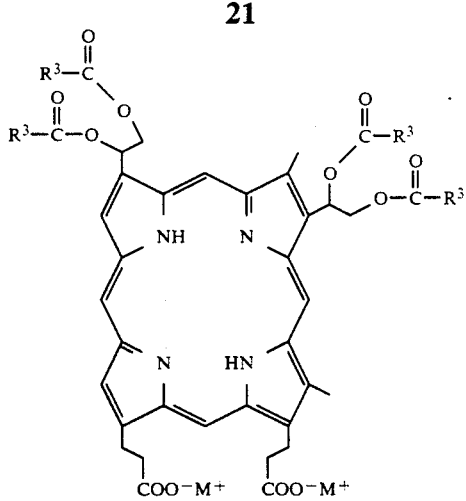
where $R^3$ is 1,2-icosahdedral closo-carborane or substituted or unsubstituted 1,7-icosahedral closo-carborane, $R^3$ substituted or unsubstituted is enriched in boron-10 wherein the substituent is a carboxyl group and $M^+$ is a physiologically acceptable salt.
* * * * *

UNITED STATES PATENT AND TRADEMARK OFFICE
CERTIFICATE OF CORRECTION

PATENT NO. : 5,149,801

DATED : SEPTEMBER 22, 1992

INVENTOR(S) : KAHL ET AL.

It is certified that error appears in the above-identified patent and that said Letters Patent is hereby corrected as shown below:

Column 5, lines 11-30, in the specification — Delete the structure shown and replace with

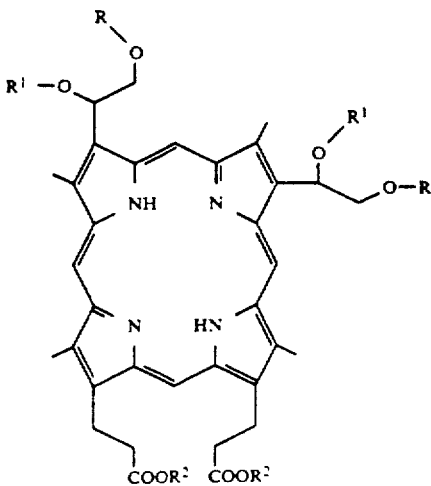

UNITED STATES PATENT AND TRADEMARK OFFICE
CERTIFICATE OF CORRECTION

PATENT NO. : 5,149,801

DATED : SEPTEMBER 22, 1992

INVENTOR(S) : Kahl et al.

Page 2 of 4

It is certified that error appears in the above-identified patent and that said Letters Patent is hereby corrected as shown below:

Column 6, lines 48-68, in the specification

Delete the structure shown and replace with

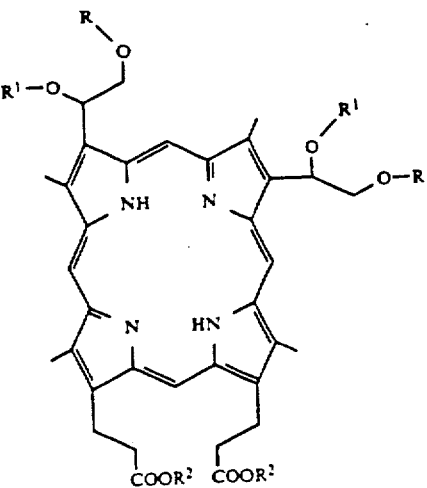

UNITED STATES PATENT AND TRADEMARK OFFICE
CERTIFICATE OF CORRECTION

PATENT NO. : 5,149,801                             Page 3 of 4
DATED      : SEPTEMBER 22, 1992
INVENTOR(S): Kahl et al.

It is certified that error appears in the above-identified patent and that said Letters Patent is hereby corrected as shown below:

Column 20, lines 16-36,    Delete the structure shown and
  claim 1                    replace with

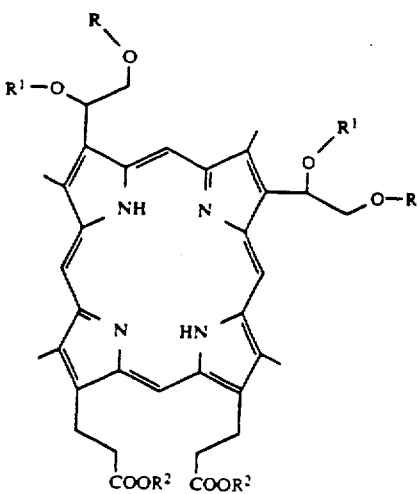

Column 20, line 51,        Delete the word "about"
  claim 1

UNITED STATES PATENT AND TRADEMARK OFFICE
CERTIFICATE OF CORRECTION

PATENT NO. : 5,149,801

DATED : SEPTEMBER 22, 1992

INVENTOR(S) : Kahl et al.

It is certified that error appears in the above-identified patent and that said Letters Patent is hereby corrected as shown below:

Column 21, lines 1-20, claim 7

Delete the structure shown and replace with

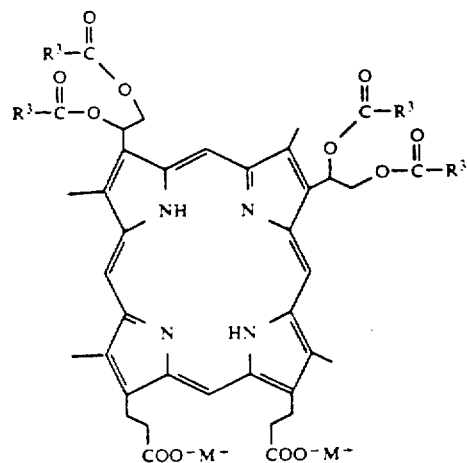

Signed and Sealed this

Twenty-eighth Day of December, 1993

Attest:

BRUCE LEHMAN

Attesting Officer

Commissioner of Patents and Trademarks